(12) United States Patent
Harhen (10) Patent No.: US 6,190,330 B1
(45) Date of Patent: Feb. 20, 2001

(54) ENDOSCOPIC LOCATION AND VACUUM ASSEMBLY AND METHOD

(75) Inventor: E. Paul Harhen, Duxbury, MA (US)

(73) Assignee: Vision-Sciences, Inc., Natick, MA (US)

( * ) Notice: Under 35 U.S.C. 154(b), the term of this patent shall be extended for 0 days.

(21) Appl. No.: 09/370,563

(22) Filed: Aug. 9, 1999

(51) Int. Cl.$^7$ ................................................. A61B 10/00
(52) U.S. Cl. .............................................................. 600/566
(58) Field of Search ................................... 600/565, 566, 600/424, 104; 128/897

(56) References Cited

U.S. PATENT DOCUMENTS 5,486,154 * 1/1996 Kelleher ................................. 600/104
5,829,444 * 11/1998 Ferre et al. ............................ 128/897
5,967,980 * 10/1999 Ferre et al. ............................ 600/424

\* cited by examiner

*Primary Examiner*—Max Hindenburg
*Assistant Examiner*—Brian Szmal
(74) *Attorney, Agent, or Firm*—Dorsey & Whitney LLP (57) ABSTRACT

An endoscopic assembly usable with an external first location indicator to assist an operator in positioning a distal end of the assembly at a desired location within a patient and creating a partial vacuum at or collecting a sample from the desired location during an endoscopic procedure, and a method for creating a partial vacuum at or collecting a sample from the desired location within the patient, are shown and described. In one embodiment, the endoscopic assembly has an elongated member and a second position indicator component. The elongated member has a distal end configured to be inserted into the patient and a proximal end portion. A bore extends from the proximal end portion of the elongated member to its distal end. The second position indicator component is sized to slidably engage the bore of the elongated member. The operator can manipulate the second position indicator component to move the position indicator component between first and second positions. In the first position, the second position indicator component is substantially adjacent to the distal end of the elongated member and communicates with the first position indicator component to aid the operator in positioning the distal end of the elongated member at the desired location within the patient. In the second position, the second position indicator component is spaced from the distal end of the elongated member toward the proximal end portion to create a void between the second position indicator component and the distal end of the elongated member. The second position indicator component is conformed to the internal surface of the bore to create a partial vacuum near the distal end of the elongated member at the desired location when the second location indicator is moved from the first position to the second position.

37 Claims, 5 Drawing Sheets

ENDOSCOPIC LOCATION AND VACUUM ASSEMBLY AND METHOD

TECHNICAL FIELD

The invention relates to surgical, therapeutic and diagnostic equipment and, more particularly, to endoscopes and endoscopic accessories.

BACKGROUND OF THE INVENTION

The use of intrabody medical equipment, such as endoscopes, catheters, and the like, for surgical, diagnostic and therapeutic purposes is rapidly expanding. To improve performance, the equipment has been optimized to best accomplish selected purposes. For example, endoscopes have been optimized and refined to provide upper endoscopes for examination of the esophagus, stomach, and duodenum; colonoscopes for the colon; angioscopes for blood vessels; bronchoscopes for the bronchi; laparoscopes for the peritoneal cavity; arthroscopes for joint spaces; nasopharyngoscopes for nasal passages and the pharynx; and intubation scopes for a person's airway.

Figure 1:
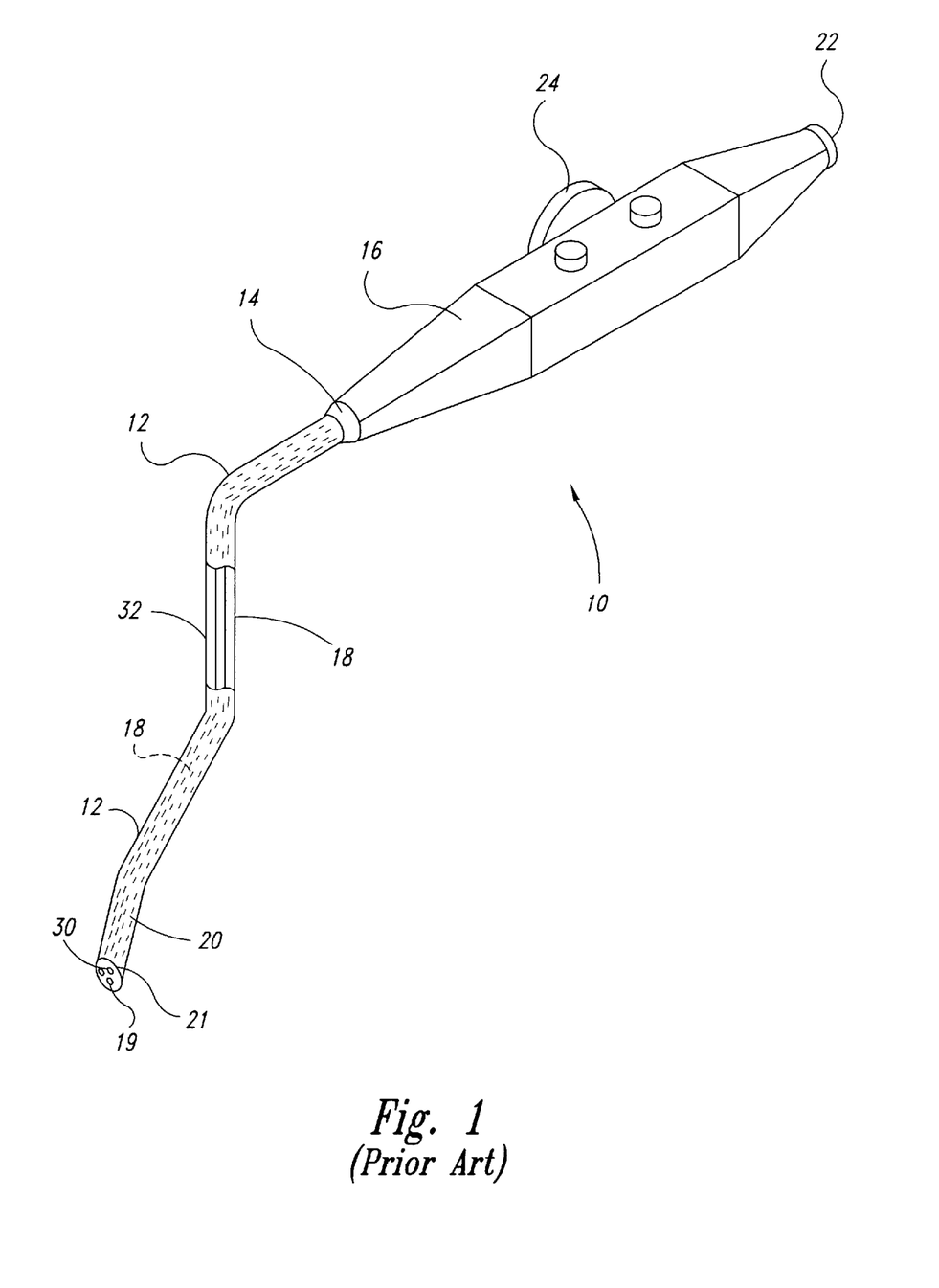
FIG. 1 is an isometric view of a prior art endoscope.

A conventional endoscopic system 10, shown in FIG. 1, has an insertion tube 12 that is connected at a proximal end 14 to a handle or headpiece 16. The insertion tube 12 is adapted to be inserted into a patient's body to perform a selected surgical, therapeutic or diagnostic procedure. The endoscopic system 10 is generally manufactured with either a rigid or flexible insertion tube 12. The rigid insertion tube 12 maintains its shape to allow the operator to change the position of the portion of the insertion tube 12 that is within the body by applying torque to the portion of the endoscopic system 10 that is outside the body. The flexible insertion tube 12, on the other hand, cannot be controlled in such a manner. Instead, control wheels 24 are mounted on the headpiece 16 and connected to the insertion tube's distal end 20 by control cables (not shown). The control wheels 24 are manipulated to bend the insertion tube's distal end 20 to move the distal end 20 up, down, left, or right. Accordingly, the distal end 20 can be controlled to allow improved visibility or positioning of working tools within the patient's body.

The insertion tube 12 often contains an imaging system 18 having optical fibers or the like extending along the length of the insertion tube and terminating at a viewing window 19 in the insertion tube's distal end 20. The imaging system 18 conveys an image from the viewing window 19 to an eyepiece 22 on the headpiece 16, or to a monitor (not shown), so the user can see into a selected body cavity during an endoscopic procedure. Through manipulation of the control wheels 24, an operator can cause the distal end 20 of the insertion tube 12 to become substantially linear, or to take a curved shape to selectively position the viewing window 19.

The endoscopic system 10 also has an elongated working channel 32 extending from the proximal end 14 to the distal end 20 of the insertion tube 12. The working channel 32 is hollow along its length, and terminates in an opening 30 at the distal end 20 of the insertion tube 12. A working tool, such as a biopsy needle (not shown), to be used in a particular procedure is inserted into the working channel 32 from the proximal end 14 of the insertion tube 12 and threaded through the working channel 32. The working tool is manipulated at the headpiece 16 external to the patient to selectively project from the working channel's opening 30 in the patient during a procedure, such as when collecting samples of tissue. The working channel 32 can also be used to inject fluid into the patient or to create suction during a procedure. The endoscopic system 10 is described in greater detail in U.S. Pat. No. Re 34,110 and U.S. Pat. No. 4,646,722, which are incorporated herein by reference.

The illustrated endoscopic system 10, however, may not be suitable for all types of procedures. A cardiac catheter, for example, may be too narrow to contain both the working channel and imaging system, and may consequently be designed without an imaging system. The operator using such a cardiac catheter typically performs the procedure without direct visualization. The operator instead performs the procedure while the patient undergoes fluoroscopy, or with the help of an assistant, such as a cytologist, who performs cell assays on site to help determine whether the operator has located the desired area for the procedure.

Miniature location sensors have been developed to attach to the distal end of cardiac catheters and neuro probes to provide the operator with indirect visualization to determine the location of the distal end of the device inside the patient during the procedure. In indirect visualization, real time location information from the sensor is superimposed over a previously acquired CT or MRI model to illustrate to the operator the location of the distal end of the insertion tube with respect to the patient. Examples of such indirect visualization systems are described in more detail in U.S. Pat. Nos. 5,546,951 and 5,568,809, which are incorporated herein by reference.

SUMMARY OF THE INVENTION

The present invention is directed to an endoscopic assembly and methods of using the endoscopic assembly that overcome deficiencies experienced in the prior art. The endoscopic assembly is adapted to assist an operator having a first position indicator component in accurately monitoring the location of a distal end of an accessory within a patient and to create a partial vacuum at or collect a sample from a specific, identified location in the patient during an endoscopic procedure.

The endoscopic assembly has an elongated member and a second position indicator component, such as a sensor, transmitter or other homing device. The second position indicator component communicates with the first position indicator component external to the patient to aid the user in positioning the distal end of the assembly within the patient. The elongated member has a distal end insertable into the patient and a proximal end portion configured to remain external to the patient during the procedure. A bore extends from the proximal end portion of the elongated member to its distal end. The second position indicator component is sized to slidably engage the bore of the elongated member. The second position indicator component can be manipulated by the operator from the proximal end portion of the elongated member to move within the bore between first and second positions. In the first position, the second position indicator component is substantially adjacent to the distal end of the elongated member and is adapted to aid the operator in identifying and monitoring the position of the distal end of the elongated member inside the patient to facilitate placement of the distal tip near the desired location. In the second position, the second position indicator component is proximally spaced from the distal end of the elongated member to create a void between the second position indicator component and the distal end of the elongated member. The second position indicator component is conformed to the internal surface of the bore such that, when the second position indicator component is moved from the first position to the second position, the partial vacuum is generated in the bore near the distal end of the elongated member at the desired location. When the distal end of the elongated member is at the desired location in the patient and the partial vacuum is generated, samples such as liquid or solid material can be drawn into and retained in the elongated member's bore.

The endoscopic assembly can alternatively be used to collect multiple samples from one or more locations in the patient by collecting a first sample in the manner described above, then collecting an additional sample by moving the second position indicator component from the second position proximally to a third position to create a partial vacuum at the open distal end of the elongated member and draw the additional sample into the open distal end. The endoscopic assembly can further collect additional samples by sequentially moving the second position indicator component proximally.

DETAILED DESCRIPTION OF THE INVENTION

The present detailed description is generally directed toward endoscopic medical devices used to locate a desired location within a patient and to create a partial vacuum at or collect a sample from the desired location, and toward methods for doing the same. Many specific details of certain embodiments of the invention are set forth in the following description and in FIGS. 2–9 to provide a thorough understanding of such embodiments. One skilled in the art, however, will understand that the present invention may have additional embodiments, or that the invention may be practiced without several of the details described in the following description.

Figure 2:
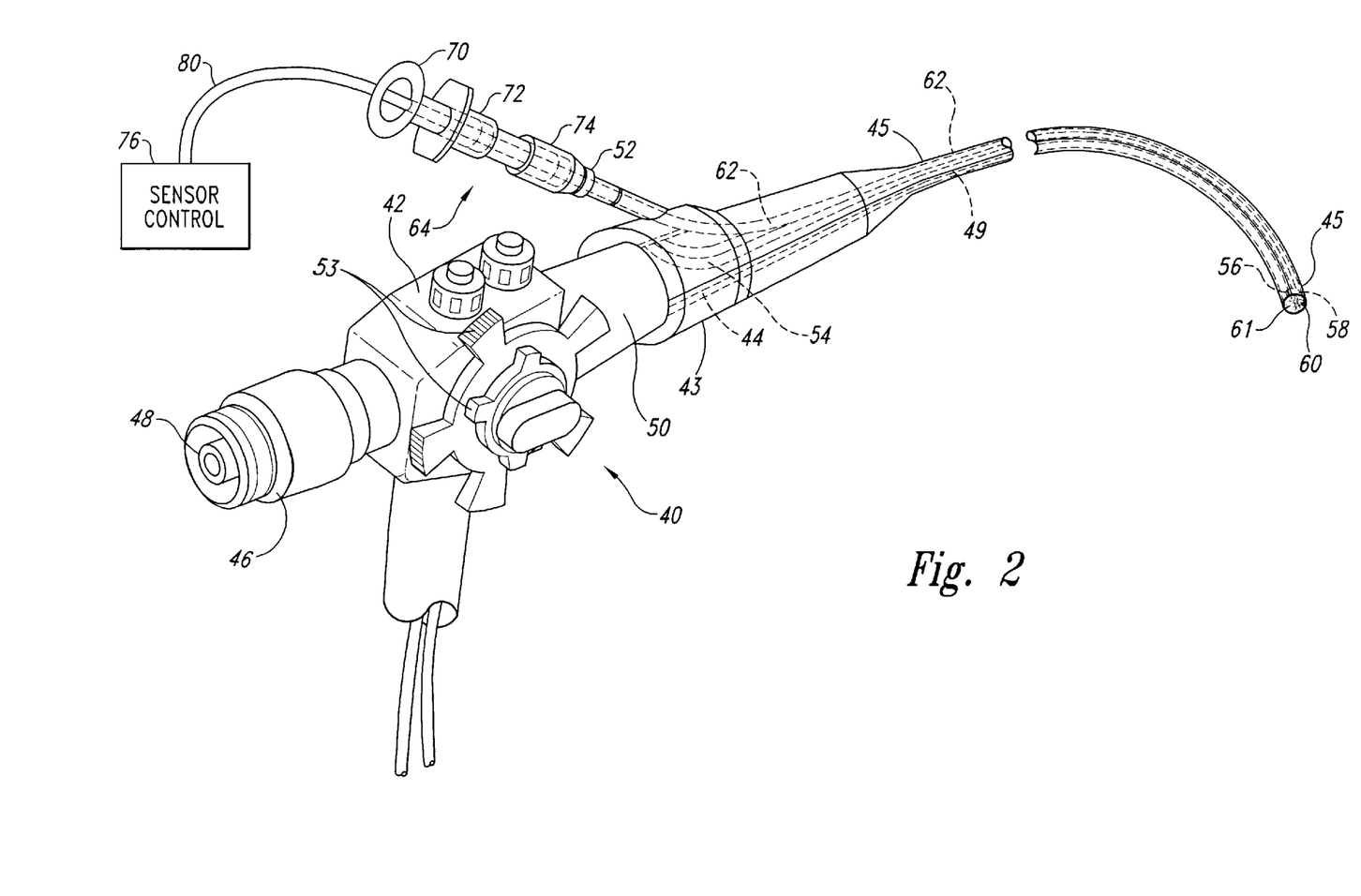
FIG. 2 is an isometric view of an endoscope and a location and vacuum assembly according to one embodiment of the present invention.

FIG. 2 illustrates an endoscope 40 and a locating and vacuum assembly 64 according to one particular embodiment of the present invention. The endoscope 40 has a headpiece 42 that remains external to the patient and is manipulable by an operator during an endoscopic procedure. The headpiece 42 is connected to an insertion tube 44 sized to be inserted into the patient during the procedure. The insertion tube 44 can be rigid or flexible. In the illustrated embodiment, the insertion tube 44 is contained within a sheath 45 isolating the insertion tube 44 from the patient during the procedure.

In the illustrated embodiment, the headpiece 42 has a first end 46 terminating in an eyepiece 48, and an opposing second end 50. The eyepiece 48 is connected to an optical system 49 to allow the operator to view the area being operated upon during the procedure. The second end 50 is attached to the insertion tube 44. The sheath 45 fits closely over the insertion tube 44, and terminates at a proximal fitting 43 shaped to receive the second end 50 of the headpiece 42. In the illustrated embodiment, the insertion tube 44 is flexible and controllable by a number of bending controls 53 on the headpiece 42. The proximal fitting 43 on the sheath 45 has a working port 52 designed to receive a working tool, such as the locating and vacuum assembly 64. The working port 52 is angled with respect to the headpiece 42 to direct the working tool toward a working channel 62 within the sheath 45. The working channel 62 extends between the working port 52 and an end cap 58 at a distal end 47 of the sheath 45.

The insertion tube 44 in the illustrated embodiment has a proximal end 54 and a distal end 56. The proximal end 54 of the insertion tube 44 is connected to the second end 50 of the headpiece 42. The distal end 56 of the insertion tube 44 terminates within the end cap 58. The end cap 58 has an opening 60 through which the working tool or a portion of the locating and vacuum assembly 64 can project during the procedure, and a viewing window 61 through which the optical system 49 can transmit images of the procedure to the eyepiece 48. The working channel 62 is sealed at the opening 60 and the working port 52 so the endoscope's insertion tube 44 is fully isolated from bodily fluids from the patient during the procedure. The locating and vacuum assembly 64 can also be used in combination with an insertion tube 44 not contained within a sheath 45. In such a case, the working channel 62 may be located within the insertion tube 44.

Figure 3:
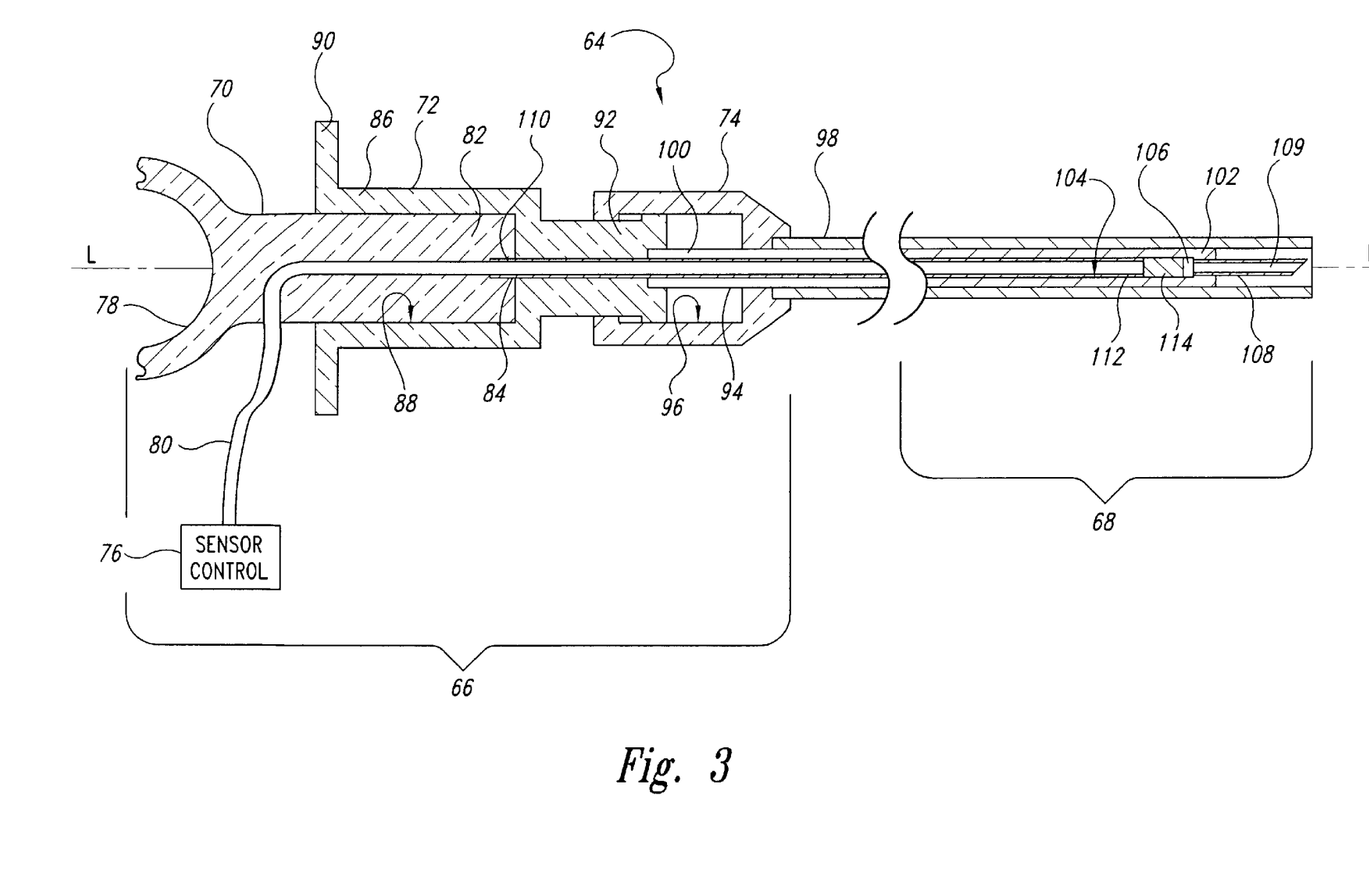
FIG. 3 is an enlarged cross-sectional view of the location and vacuum assembly of FIG. 2.

The locating and vacuum assembly 64 has an external portion 66 and an insertion portion 68 (FIG. 3). The external portion 66 remains external to the patient during the procedure and the insertion portion 68 is inserted through the working port 52 and into the working channel 62 during the procedure. The external portion is made up primarily of a sensor actuator 70, a housing 72, a cover actuator 74 and a sensor control 76. As discussed in detail below, the sensor actuator 70 is slidably engaged with the housing 72 and the housing 72 is slidably engaged with the cover actuator 74 to manipulate the insertion portion 68 of the locating and vacuum assembly 64 during the procedure.

As best illustrated in FIG. 3, the sensor actuator 70 has a handle 78 at an end most proximal with respect to the operator during use, and a distal end 82. The sensor actuator 70 slides axially along the longitudinal axis L—L with respect to the housing 72. The distal end 82 of the sensor actuator 70 is sized and shaped to mate with the housing 72. Wiring 80 extends through the sensor actuator 70 and is operatively connected at one end to the sensor control 76. The wiring 80 also extends distally from the sensor actuator 70 beyond its distal end 82. The wiring 80 is fixed to the sensor actuator 70 to move axially with the sensor actuator with respect to the remainder of the locating and vacuum assembly 64.

A sensor coupling 84 is coaxially oriented with respect to the longitudinal axis L—L around the outside of the wiring 80 and is attached to the distal end 82 of the sensor actuator 70. The sensor coupling 84 is also fixed to the sensor actuator 70 to move with the sensor actuator and the wiring 80 as a unit. In the illustrated embodiment, the handle 78 is an oval loop (FIG. 2) and the distal end 82 of the sensor actuator 70 is substantially cylindrical. The handle 78 and distal end 82, however, can each have different shapes.

The housing 72 is engaged with the distal end 82 of the sensor actuator 70. The housing 72 has a proximal end 86 and an opposing distal end 92. The proximal end 86 engages the sensor actuator 70 and the distal end 92 similarly engages the cover actuator 74. The proximal end 86 terminates in a flange 90 to facilitate the operator in moving the sensor actuator 70. The housing 72 has an internal first socket 88 sized and shaped to slidably receive the distal end 82 of the sensor actuator 70. In the illustrated embodiment, the first socket 88 is substantially cylindrical to complement the cylindrical sensor actuator 70. The first socket 88, however, can have a wide variety of shapes to mate with the sensor actuator 70. The distal end 92 of the housing 72 is also substantially cylindrical to mate with the cover actuator 74. The sensor coupling 84, along with the wiring 80 internal to it, extend from the first socket 88 through the housing 72 and out its distal end 92. The sensor coupling 84 is movable axially within the housing 72 along the longitudinal axis L—L. Axial movement of the sensor actuator 70 with respect to the housing 72 therefore causes the sensor coupling 84 and the wiring 80 to slide axially through the housing 72. An elongated tubular member 94 is attached to the distal end 92 of the housing 72. The elongated member 94 is concentrically oriented about the longitudinal axis L—L and radially outward of the sensor coupling 84. The elongated member 94 is fixed to the distal end 92 of the housing 72 and the sensor coupling 84 is slidable within the elongated member.

The cover actuator 74 has a second socket 96 sized and shaped to slidably receive the distal end 92 of the housing 72. In the illustrated embodiment, the distal end 92 of the housing 72 and the complementary second socket 96 are both substantially cylindrical. The distal end 92 and the second socket 96, however, can have a wide variety of shapes. The distal end 92 of the housing 72 has an annular shoulder 93 positioned within the second socket 96. The proximal end of the cover actuator 74 also has an annular shoulder 95 positioned to engage the housing's annular shoulder 93 when the housing 72 is moved proximally a selected distance relative to the cover actuator 74.

The elongated member 94, along with the sensor coupling 84 and the wiring 80 internal to it, slidably extend through the cover actuator 74. Movement of the housing 72 along the longitudinal axis L—L with respect to the cover actuator 74 therefore causes the elongated member 94 to slide axially with respect to the cover actuator. A protective cover 98 is attached at its proximal end to the cover actuator 74. The protective cover 98 is concentrically positioned about the longitudinal axis L—L and radially outward of the elongated member 94. The elongated member 94 is slidable within the protective cover 98. Movement of the cover actuator 74 along the longitudinal axis L—L with respect to the housing 72 therefore causes the elongated member to slide axially within the protective cover 98.

The insertion portion 68 of the locating and vacuum assembly 64 includes the distal portions of the protective cover 98, the elongated member 94, the sensor coupling 84 and the wiring 80. The elongated member 94 has a proximal end 100 attached to the housing 72, a distal end 102 opposite the proximal end, and an internal surface 104 that defines a bore 106 that slidably receives the sensor coupling 84. The distal end 102 of the elongated member 94 is attached to a biopsy needle 108. In the illustrated embodiment, the biopsy needle 108 is coaxially oriented with respect to the longitudinal axis L—L within the elongated member's distal end 102, and is attached to the internal surface 104 of the elongated member 94. The biopsy needle 108 is hollow with a channel 109 extending substantially along the longitudinal axis L—L. The channel 109 opens at one end at the biopsy needle's sharp distal end, and opens at its proximal end into the bore 106 within the elongated member 94.

The sensor coupling 84 within the elongated member 94 has a distal end 112 attached to a first position indicator component, such as a sensor 114. The sensor 114 is sized and shaped to fit within the bore 106 and to closely conform to the elongated member's internal surface 104. The sensor 114 can also be smaller than the bore 106, but surrounded by a resilient material such as a seal to closely conform the sensor 114 to the internal surface 104 so as to form a seal therebetween.

Figure 4:
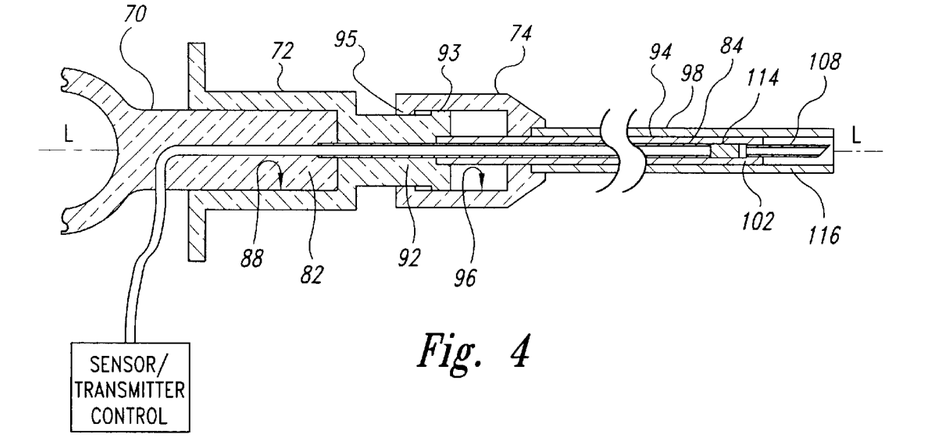
FIGS. 4–6 are reduced, cross-sectional views of the location and vacuum assembly of FIG. 3 in different configurations.
Figure 5:
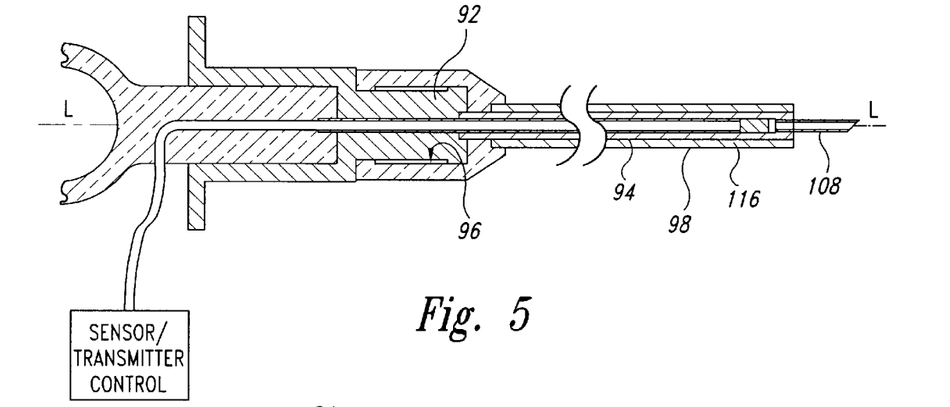
Figure 6:
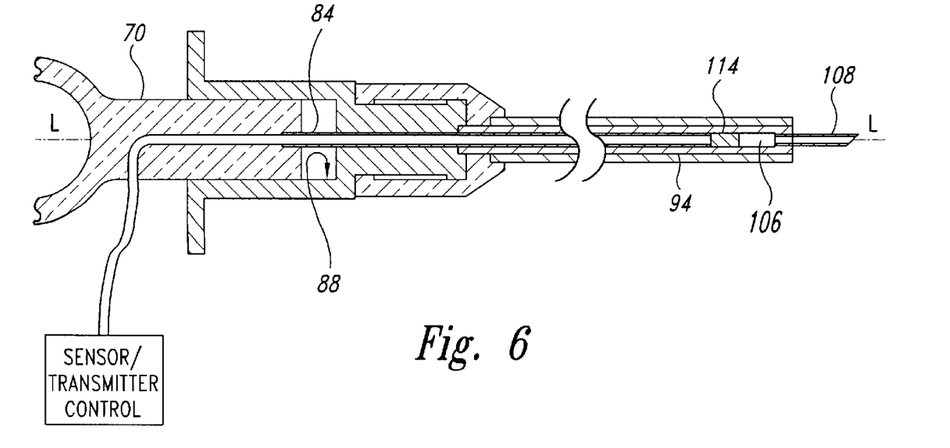

FIGS. 4–6 illustrate the above embodiment of the location and vacuum assembly 64 during operation. In FIG. 4, the sensor actuator 70 is fully engaged with the housing 72 such that the distal end 82 of the sensor actuator 70 is completely within the first socket 88. The housing 72 is only partially engaged with the cover actuator 74. The distal end 92 of the housing 72 is retracted from the second socket 96 by a sufficient distance to cause a distal end 116 of the protective cover 98 to project beyond the entire biopsy needle 108. Because the sensor actuator 70 is fully engaged with the housing 72, the sensor 114 is fully extended to a point near the distal end 102 of the elongated member 94. In this configuration, the locating and vacuum assembly 64 is prepared to be inserted into an endoscope's working channel or directly into a patient. The distal end 116 of the protective cover 98 prevents the biopsy needle 108 from contacting the patient during the insertion process. The sensor 114 communicates with the sensor control 76 which calculates the specific location of the sensor 114 relative to the patient to assist the operator in placing the sensor and biopsy needle 108 at a desired location within the patient. In this configuration, the locating and vacuum assembly 64 can be inserted into the patient with the endoscope's insertion tube as a unit, or the assembly can be inserted into the working port 52 and working channel 62 of the endoscope 40 or sheath 45 as illustrated in FIG. 2 after the insertion tube is already in the patient. Once the locating and vacuum assembly 64 is inserted to the desired location within the patient, the locating and vacuum assembly can be actuated to collect a sample of tissue or fluid from the desired location.

In FIG. 5, the locating and vacuum assembly 64 is configured to collect a sample from within the patient. The locating and vacuum assembly 64 is in the same configuration as shown in FIG. 4, except in FIG. 5 the cover actuator 74 is fully engaged with the housing 72, so the distal end 92 of the housing 72 is fully inserted into the second socket 96 of the cover actuator 74. As the housing 72 is moved axially into the cover actuator 74, the elongated member 94 and the biopsy needle 108 are slid axially in the protective cover 98 until the biopsy needle is projected beyond the distal end of the protective cover. In this configuration, the biopsy needle 108 projects beyond the viewing window 61 by a sufficient distance to allow the operator to optically view the biopsy needle through the endoscope's insertion tube 44 while the precise location of the biopsy needle 108 relative to the patient's body is identified via the sensor 114 and the sensor control 76. The biopsy needle 108 is then manipulated to receive a sample from the desired location within the patient.

In FIG. 6, the locating and vacuum assembly 64 is configured to collect the selected sample via the biopsy needle 108. The sensor actuator 70 is partially retracted from the first socket 88 to draw the sensor coupling 84 and the attached sensor 114 proximally within the bore 106 of the elongated member 94 along the longitudinal axis L—L away from the biopsy needle 108. As the sensor 114 moves proximally within the elongated member 94, a partial vacuum is formed in the portion of the bore 106 distal to the sensor 114. This partial vacuum creates a reduced pressure within the channel 109 of the biopsy needle 108 which draws a sample into the biopsy needle 108. In one embodiment, the sensor actuator 70 has indicia printed on it, adhered to it, or otherwise formed thereon. The indicia is visible to the user as the sensor actuator is retracted from the first socket 88. The indicia provides the user with an indication of how far the sensor 114 has been withdrawn to create the vacuum. The indicia can be calibrated to indicate the distance that the sensor 114 has moved from its distal most position, or to indicate an estimated volume of a collected sample as the sensor is retracted. The indicia can also be calibrated to indicate how far the sensor actuator is to be moved to capture multiple tissue or fluid samples.

In one embodiment, the elongated member 94 and the biopsy needle 108 are moved as a unit to a selected location, and the sensor 114 is then moved proximally within the bore to collect a first sample through the biopsy needle 108 and into the elongated member's distal end 116. The elongated member 94 and biopsy needle 108 are then moved to another selected location, and the sensor 114 is moved proximally again within the elongated member 94. As the sensor 114 is moved proximally, the first sample also moves proximally and a second sample is drawn into the bore 106 of the elongated member 94 adjacent to the first sample. This process can be repeated multiple times so as to collect multiple distinct specimens within the bore 106 of the elongated member 94 without having to use multiple endoscopic accessories to take biopsy samples. The multiple samples can also be easily removed from the elongated member after the endoscopic procedure and analyzed individually as needed.

Figure 7:
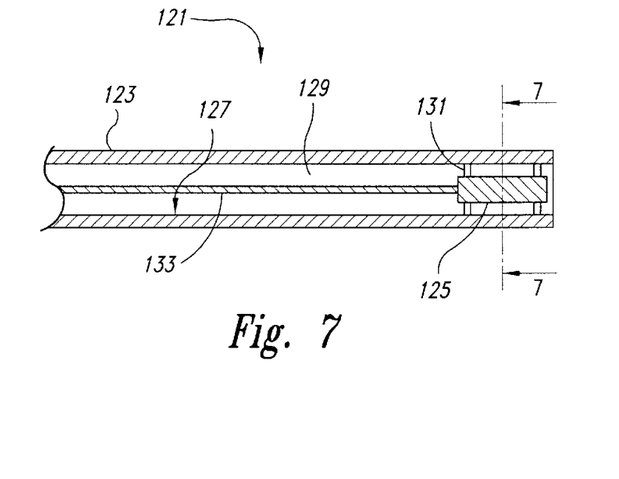
FIG. 7 is a cross-sectional view of a distal end of an insertion tube of another location and vacuum assembly according to another embodiment of the present invention.
Figure 8:
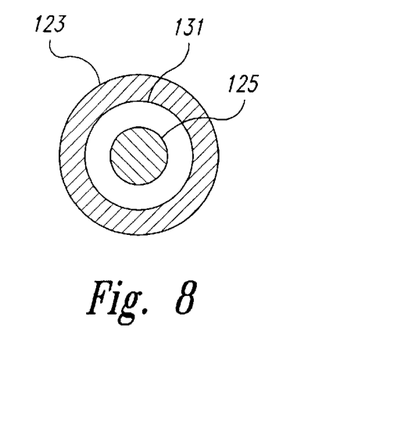
FIG. 8 is a cross-sectional view taken substantially along line 8—8 of FIG. 7.

FIGS. 7 and 8 illustrate an alternate embodiment of the location and vacuum assembly. In FIG. 7 an insertion portion 121 is shown having an elongated member 123 and a sensor 125 oriented within the elongated member. The elongated member 123 has an internal surface 127 that defines a bore 129 extending along the entire elongated member. The sensor 125 is sized and shaped to fit within the bore 129 of the elongated member 123. The sensor 125 has at least one seal 131 sized and shaped to closely conform to the internal surface 127 of the elongated member 123. A wire 133 is connected to the sensor 125. The wire 133 can be manipulated by the operator to move the sensor 125, and may also contain electrical wiring (not shown) to communicate with the sensor control 76 to aid the operator in locating a desired location within the patient. When the operator manipulates the wire 133 to move the sensor 125 proximally, the movement of the sensor 125 and the seal 131 creates a localized area of reduced pressure distal to the sensor 125. This reduced pressure can be used to draw fluid to collect a sample from the patient into the elongated member 123. Multiple samples can also be collected with the location and viewing assembly 141 of this alternate embodiment.

Figure 9:
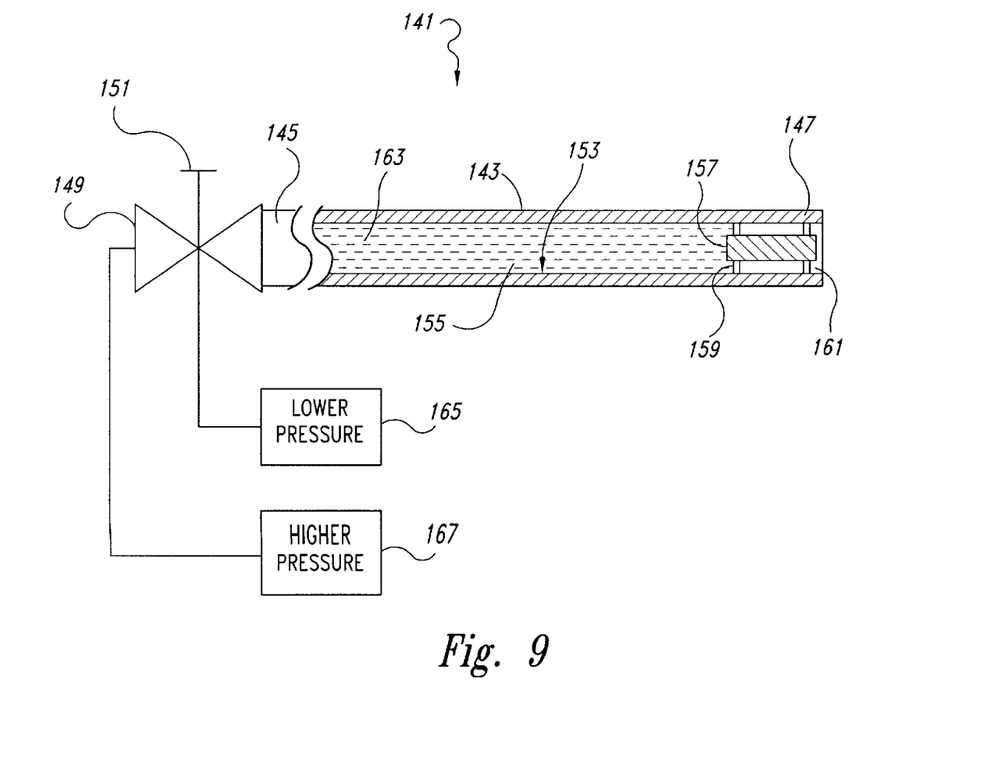
FIG. 9 is a partial cross-sectional view of another location and vacuum assembly according to another alternate embodiment of the present invention, a distal end of the assembly being shown in cross-section and a proximal end of the assembly being shown schematically.

FIG. 9 illustrates another alternate embodiment of the location and vacuum assembly 141. The location and vacuum assembly 141 has an elongated member 143 having a proximal end 145 and a distal end 147. The proximal end 145 of the elongated member 143 is connected to a valve 149 having an actuator 151. The elongated member 143 has an internal surface 153 defining a bore 155. A sensor 157 is sized and shaped to fit within the bore 155 of the elongated member 143. The sensor has a first seal 159 and a second seal 161 sized and shaped to closely conform to the internal surface 153 of the elongated member 143. The portion of the bore 155 proximal to the first seal 159 is filled with a working fluid 163, such as water or air. The first seal 159 prevents the working fluid 163 from passing by the sensor 157. The valve 149 is independently connected to two pressure sources: a source of lower pressure 165 and a source of higher pressure 167. These sources are higher and lower, respectively, than the working fluid 163 in the bore 155. The valve 149 is configured to selectively connect the bore 155 with either the source of lower pressure 165 or the source of higher pressure 167. The valve can also be closed to prevent the working fluid 163 from entering or leaving the bore 155.

During operation, the operator manipulates the actuator 151 on the valve 149 to cause the working fluid 163 to enter or exit the bore 155 and move the sensor 157 axially within the elongated member 143. Movement of the sensor 157 proximally creates a location of reduced pressure near the distal end 147 of the elongated member 143. By connecting the bore 155 with the source of lower pressure 165, the operator reduces the pressure of the working fluid 163 within the bore which moves the sensor 157 proximally to create an area of reduced pressure at the distal end 147 of the elongated member 143. This area of reduced pressure can draw fluid or solid material into the elongated member 143 to collect one or more samples from the patient. The operator can also connect the bore 155 to the source of higher pressure 167 to move the sensor 157 distally with respect to the elongated member 143. This distal movement of the sensor 157 will eject either the fluid or the sample from the bore 155 of the elongated member 143. Accordingly, distal movement of the sensor 157 can act to place selected material into the patient at predetermined locations, or the sensor 157 can be moved distally to eject the samples from the elongated member after the assembly is removed from the patient.

Different embodiments of the present invention can be used to create an area of reduced pressure at the distal end of the endoscope. In contrast to traditional catheters, the present invention can create a partial vacuum at the distal tip even when used in connection with a location sensor. Embodiments of the present invention can therefore be used for both positioning the distal end of the device at a desired location within the patient and collecting fluid or samples from the desired location. In addition, embodiments of the present invention can collect multiple samples from one or more desired locations within the patient. By sequentially moving the sensor proximally, multiple samples can be taken from the patient. Once all the desired samples have been taken, the sensor can be used to eject the samples from the elongated member. After removing the elongated member from the patient, the operator can manipulate the actuator to move the sensor distally and thereby eject samples from the bore.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An endoscopic assembly usable with an external first position indicator component and for creating a partial vacuum at a desired location within the patient during an endoscopic procedure, the endoscopic assembly comprising:

an elongated member having a distal end configured to be inserted into the patient and a proximal end portion configured to remain external to the patient during the procedure, and a bore extending from the proximal end portion to the distal end; and a second position indicator component sized to slide within the bore and slidably engage the elongated member, the second position indicator component being manipulable to move within the bore between first and second positions, in the first position the second position indicator component is substantially adjacent to the distal end of the elongated member and is communicable with the first position indicator component to aid the operator in positioning the distal end of the elongated member in the patient near the desired location, in the second position the second position indicator component is spaced from the distal end of the elongated member toward the proximal end portion to create a void between the second position indicator component and the distal end of the elongated member, the second position indicator component being sized relative to the bore to create a partial vacuum near the distal end of the elongated member at the desired location when the second position indicator component is moved from the first position to the second position.

2. The endoscopic assembly of claim 1, further comprising an actuator coupled to the second position indicator component and manipulable to move the second position indicator component between the first and second positions.

3. The endoscopic assembly of claim 2, further comprising an elongated attachment member having first and second ends, the first end of the attachment member being coupled to the actuator and the second end of the attachment member being coupled to the second position indicator component.

4. The endoscopic assembly of claim 3 wherein the attachment member comprises a wire.

5. The endoscopic assembly of claim 1, further comprising an actuator coupled to the proximal end portion of the elongated member, the actuator being accessible to the operator, and a portion of the bore between the actuator and the homing device comprising a working fluid having a pressure such that the actuator is in fluid communication with the second position indicator component and is manipulable to move the second position indicator component between the first and second positions.

6. The endoscopic assembly of claim 5 wherein the working fluid is water and the actuator comprises a hydraulic reservoir.

7. The endoscopic assembly of claim 1, further comprising a biopsy needle attached to the distal end of the elongated member, the biopsy needle having a channel therethrough extending between the bore of the elongated member and a point external to the elongated member for receiving a sample from within the patient.

8. The endoscopic assembly of claim 1 wherein the elongated member is at least partially flexible.

9. The endoscopic assembly of claim 1 wherein the second position indicator component comprises a sensor.

10. The endoscopic assembly of claim 1 wherein the second position indicator component comprises a transmitter.

11. The endoscopic assembly of claim 1 wherein the bore has an internal surface and the second position indicator component has an external surface configured to sealably engage the internal surface of the bore.

12. The endoscopic assembly of claim 1 wherein the bore has an internal surface and the second position indicator component has an external surface, and further comprising at least a first sealing element attached to the second position indicator component and sealably engagable with the internal surface of the bore.

13. An endoscopic assembly usable with an external first position indicator component and for collecting a sample from a desired location within a patient during an endoscopic procedure, the endoscopic assembly comprising:

an elongated member having a proximal end portion configured to remain external to the patient during the procedure, an open distal end configured to be inserted into the patient, and a bore extending between the proximal end portion and the distal end; and a second position indicator component sized to slide within the bore and to slidably engage the elongated member, the second position indicator component being manipulable to move within the bore between first and second positions, in the first position the second position indicator component is located within the bore substantially adjacent to the distal end of the elongated member and the second position indicator component is communicable with the first position indicator component to aid the operator in positioning the distal end of the elongated member within the patient near the desired location, and in the second position the second position indicator component is spaced apart from the distal end of the elongated member toward the proximal end to create a sample collection area in the bore between the second position indicator component and the distal end of the elongated member, the second position indicator component being sized to closely fit within the bore to create a partial vacuum near the distal end of the elongated member when the second position indicator component is moved from the first position to the second position for collecting a sample from the desired location through the open distal end and retaining the sample within the sample collection area.

14. The endoscopic assembly of claim 13, further comprising an actuator coupled to the second position indicator component, the actuator being manipulable to move the second position indicator component between the first and second positions.

15. The endoscopic assembly of claim 14, further comprising an elongated attachment member having first and second ends, the first end of the attachment member being coupled to the actuator and the second end of the attachment member being coupled to the second position indicator component.

16. The endoscopic assembly of claim 15 wherein the attachment member comprises a wire.

17. The endoscopic assembly of claim 13, further comprising an actuator coupled to the proximal end portion of the elongated member, the actuator being accessible to the operator, and a portion of the bore between the actuator and the second position indicator component comprising a working fluid having a pressure such that the actuator is in fluid communication with the second position indicator component and is manipulable to move the second position indicator component between the first and second positions.

18. The endoscopic assembly of claim 17 wherein the working fluid is water and the actuator comprises a hydraulic reservoir.

19. The endoscopic assembly of claim 13, further comprising a biopsy needle attached to the distal end of the elongated member, the biopsy needle having a channel therethrough extending between the bore of the elongated member and a point external to the elongated member for receiving a sample from within the patient.

20. The endoscopic assembly of claim 13 wherein the elongated member is at least partially flexible.

21. The endoscopic assembly of claim 13 wherein the second position indicator component comprises a sensor.

22. The endoscopic assembly of claim 13 wherein the second position indicator component comprises a transmitter.

23. The endoscopic assembly of claim 13 wherein the bore has an internal surface and the second position indicator component has an external surface configured to sealably engage the internal surface of the bore.

24. The endoscopic assembly of claim 13 wherein the bore has an internal surface and the second position indicator component has an external surface, and further comprising at least a first sealing element attached to the second position indicator component and sealably engagable with the internal surface of the bore.

25. An endoscopic system usable with an external first position indicator component and for creating a partial vacuum at a desired location within a patient during an endoscopic procedure, the system comprising:
   a first elongated member having a distal end configured to be inserted into the patient and a proximal end portion configured to remain external to the patient during the procedure, the first elongated member having at least a first bore extending from the proximal end portion through the distal end;
   a second elongated member having a proximal end portion and a distal end, the second elongated member being slidably insertable into the first bore and selectively extendable beyond the distal end of the first elongated member, the second elongated member having a second bore extending from the proximal end portion to the distal end of the second elongated member; and
   a second position indicator component slidably engagable with the bore of the second elongated member, the second position indicator component being manipulable to move within the second bore between first and second positions, in the first position the second position indicator component is substantially adjacent to the distal end of the second elongated member and is communicable with the first position indicator component to aid the operator in positioning the distal end of the second elongated member in the patient to the desired location, in the second position the second position indicator component is spaced from the distal end of the second elongated member toward the proximal end portion to create a void between the second position indicator component and the distal end of the second elongated member, the second position indicator component being sized relative to the bore to create a partial vacuum near the distal end of the second elongated member at the desired location when the second position indicator component is moved from the first position to the second position.

26. The endoscopic system of claim 25 wherein the first elongated member comprises a sheath, and wherein the bore of the first elongated member comprises a working channel extending from the distal end to the proximal end portion of the sheath.

27. A method for creating a partial vacuum at a desired location within a patient, the method comprising:
   providing an elongated member having proximal end portion, an open distal end and a bore extending therebetween;
   positioning a position indicator component within the bore of the elongated member and substantially adjacent to the open distal end;
   inserting the elongated member and the position indicator component into the patient;
   detecting the position of the position indicator component within the patient relative to a selected location in the patient;
   moving the position indicator component and the open distal end of the elongated member as a unit to the desired location within the patient; and
   creating the partial vacuum at the desired location by moving the position indicator component within the bore proximally away from the open distal end and toward the proximal end portion of the elongated member to create the partial vacuum in the bore near the open distal end of the elongated member at the desired location as the position indicator component moves from the first position to the second position.

28. The method of claim 27, further comprising the step of positioning the elongated member in a working channel of an endoscopic assembly.

29. The method of claim 28 wherein the endoscopic assembly comprises a sheath insulating the elongated member from the patient.

30. The method of claim 28 wherein the elongated member is positioned in the working channel of the endoscopic assembly before the endoscopic assembly is inserted into the patient.

31. The method of claim 27, further comprising an actuator coupled to the position indicator component, and wherein moving the position indicator component within the bore comprises manipulating the actuator from a position external to the patient and drawing the position indicator component axially within the bore toward the proximal end of the elongated member to create a void in the bore adjacent to the open distal end.

32. The method of claim 27, further comprising an actuator coupled to the proximal end portion of the elongated member, and wherein the bore between the actuator and the position indicator component contains a working fluid having a pressure such that the actuator is in fluid communication with the position indicator component, and wherein moving the position indicator component within the bore comprises manipulating the actuator to decrease the pressure in the working fluid between the actuator and the position indicator component and drawing the position indicator component axially within the bore toward the proximal end portion of the elongated member to create a void in the bore adjacent to the open distal end.

33. The method of claim 27 wherein the bore has an internal surface and the position indicator component has an external surface, and wherein positioning the position indicator component within the bore comprises sealably engaging the external surface of the position indicator component with the internal surface of the bore.

34. A method for positioning a distal end of an endoscopic device at a desired location within a patient and collecting at least a first sample from the desired location, the method comprising:
   providing an elongated member having proximal end portion, an open distal end and a bore extending therebetween;
   positioning a position indicator component within the bore of the elongated member in a first position substantially adjacent to the open distal end;
   detecting the position of the desired location within the patient;
   detecting the position of the position indicator component;

inserting the elongated member and the position indicator component into the patient;

moving the position indicator component and the open distal end of the elongated member as a unit to the desired location within the patient;

collecting samples by moving the position indicator component within the bore proximally away from the first position and to a second position toward the proximal end portion of the elongated member; and drawing the first sample into the bore from the desired location as the position indicator component is moved from the first position to the second position.

35. The method of claim 34, further comprising an actuator coupled to the position indicator component, and wherein moving the position indicator component within the bore between the first and second positions comprises manipulating the actuator from a position external to the elongated member and drawing the position indicator component axially within the bore toward the proximal end of the elongated member to create a void in the bore adjacent to the open distal end.

36. The method of claim 34, further comprising an actuator coupled to the proximal end portion of the elongated member, the actuator being at least partially accessible to the operator, a portion of the bore between the actuator and the position indicator component containing a working fluid having a pressure such that the actuator is in fluid communication with the position indicator component, and wherein moving the position indicator component within the bore between the first and second positions comprises manipulating the actuator to decrease the pressure in the working fluid between the actuator and the position indicator component and drawing the position indicator component axially within the bore toward the proximal end portion of the elongated member to create a void in the bore adjacent to the open distal end.

37. The method of claim 34 for further collecting at least a second sample, further comprising moving the position indicator component within the bore proximally away from the second position and to a third position toward the proximal end portion of the elongated member to create the partial vacuum in the bore adjacent to the open distal end of the elongated member at the desired location for drawing the first sample into the bore from the desired location.

\* \* \* \* \*